(12) United States Patent
Park et al.

(10) Patent No.: US 7,179,600 B2
(45) Date of Patent: Feb. 20, 2007

(54) OLIGONUCLEOTIDE CHIP COMPOSITION AND A METHOD FOR ANALYZING A HEPATITIS C VIRUS GENOTYPE USING THE COMPOSITION

(75) Inventors: Young-Suk Park, Seoul (KR); Jae-Chan Park, Seoul (KR); Eun-Ha Kim, Seoul (KR)

(73) Assignee: Biocore Co., Ltd., Seoul (KR)

( * ) Notice: Subject to any disclaimer, the term of this patent is extended or adjusted under 35 U.S.C. 154(b) by 477 days.

(21) Appl. No.: 10/475,025

(22) PCT Filed: Apr. 10, 2002

(86) PCT No.: PCT/KR02/00640

§ 371 (c)(1),
(2), (4) Date: Apr. 22, 2004

(87) PCT Pub. No.: WO02/083948

PCT Pub. Date: Oct. 24, 2002

(65) Prior Publication Data

US 2004/0170957 A1    Sep. 2, 2004

(30) Foreign Application Priority Data

Apr. 12, 2001  (KR)  .............................. 2001-19648
Jan. 8, 2002   (KR)  ................................ 2002-997

(51) Int. Cl.
*C12Q 1/00*   (2006.01)
*C12Q 1/04*   (2006.01)
*C12Q 1/68*   (2006.01)
*C12Q 1/70*   (2006.01)
*C07H 21/00*  (2006.01)
*C07H 21/04*  (2006.01)

(52) U.S. Cl. .................. 435/6; 435/4; 435/6; 536/23.1; 536/24.3; 536/24.32; 536/23.33

(58) Field of Classification Search .................... 435/4, 435/5, 6; 536/23.1, 23.72, 24.3, 24.32, 24.33
See application file for complete search history.

(56) References Cited

U.S. PATENT DOCUMENTS

| | | | |
|---|---|---|---|
| 5,550,016 A | 8/1996 | Okamoto | 435/5 |
| 5,851,759 A | 12/1998 | Weiner | 435/5 |
| 5,856,458 A | 1/1999 | Okamoto et al. | 536/24.3 |

FOREIGN PATENT DOCUMENTS

| | | |
|---|---|---|
| EP | 0 532 258 A | 3/1993 |
| EP | 0 633 321 A | 1/1995 |
| EP | 1026262 | 8/2000 |
| JP | 4-300000 | 10/1992 |
| JP | 6-125777 | 5/1994 |
| WO | WO 00/26418 A | 5/2000 |

OTHER PUBLICATIONS

Ding et al., Single-strand conformation polymorphism for analysis of genomic variability of hepatitis C virus nonstructure 5A region, *Chinese Medical Journal* 111(11):1114-7, 1998.

Makoto et al., The extremely rapid oligonucleotide hybridization and high thoughput detection of microbial gene sequences using fluorescence polarization, *Biosensors & Bioelectronics* 16:695-9, 2001.

*Primary Examiner*—Bruce R. Campbell
*Assistant Examiner*—Zachariah Lucas
(74) *Attorney, Agent, or Firm*—Jones Day

(57) ABSTRACT

The present invention discloses a method for analyzing a HCV genotype by extracting RNA from plasma and serum, performing C-type hepatitis virus (HCV) RT-PCR and then making them react on an oligonucleotide chip. The present invention also provides a method for simply and exactly examining the analysis of the HCV genotype for four people on one slide.

8 Claims, 2 Drawing Sheets

1b type

OLIGONUCLEOTIDE CHIP COMPOSITION AND A METHOD FOR ANALYZING A HEPATITIS C VIRUS GENOTYPE USING THE COMPOSITION

BACKGROUND OF THE INVENTION

1. Field of the Invention

The present invention relates to oligonucleotide chip composition and a manufacturing method thereof, and in particular, to an oligonucleotide chip composition for analyzing hepatitis C virus (HCV) genotype and detecting method thereof.

2. Description of the Prior Art

In general, hepatitis C virus (hereinafter, referred to as 'HCV'), which is a kind of hepatitis virus, is a principal factor in causing serious diseases such as hepatitis including acute hepatitis and chronic hepatitis, which may develop into hepatic cirrhosis and hepatoma. The HCV is infected via blood transfusion and fluid (Choo et al., *Science* 244, 359–362, 1989). It is estimated that about 4 hundred million people over the world are infected with the HCV: 0.2–2% of people in the developed countries such as Europe, North America and Japan; 2–5% in South America and Asia; over 5% in Africa; 1.6% in Korea (Park et al., *J. Viral Hepat.* 2, 195–202, 1995). The HCV is a very threatening virus to human health, and it is not convalescent unlike hepatitis B virus (HBV). 50–85% of the infected people develope on chronic hepatitis. Because the HCV is RNA virus, scientists have not developed any proper remedies and vaccines, much less basic study on the HCV yet. Because diagnosis methods are developed by the development of molecular biology, people can avoid the possibility of infection resulting from blood transfusion. However, because route of infection is still obscure, the possibility of infection still remains.

The HCV is positive-single strand linear RNA virus consisting of about 9,500 bases and about 3,000 amino acids, having a size of 50 nm which Choo et al. discovered in non-A or non-B (NANB) type hepatitis virus obtained from blood plasma of chimpanzee in 1989. The HCV basically consists of open reading frame (ORF) producing structural protein of core, nucleocapsid and envelope glycoprotein and unstructural protein of helicase, viral protease, RNA-dependent RNA polymerase, transcriptase and regulatory peptide (Chou et al., *Jpn. J. Med. Sci. Biol.* 4, 147–157, 1991). Both ends of ORF has 5'-untranslated region (5'UTR) and 3'UTR, respectively. 5'UTR, which is a best preserved portion in HCV gene, has about 340 bp and a stem-loop structure (Han et al., *Proc. Natl. Acac. Sci. U.S.A.* 88, 1711–1715, 1991).

Because of high mutation rate of HCV, $(1.44-1.92) \times 10^{-3}$ of base replacement in HCV is generated per year. 5'UTR and capsid of HCV gene are best preserved. Mutation generates most frequently in E1 and E2 (Ogata et al., *Proc. Natl. Acad. Sci. U.S.A.* 88, 3392–3396, 1991). Because of this property, HCV shows high gene polymorphism. Thus, up to now HCV is classified into 6 types and subtypes ranging from several to tens (Simmonds et al., *J. Gen. Virol.* 74, 2391–2399, 1993; Cha et al., *Proc. Natl. Acad. Sci. U.S.A.* 89, 7144–7148, 1992). Because there has been no standard method of classifying these types, researchers use different classification but Simmond's classification is generally used. This classification attaches figures (1, 2, 3, . . . ) on genotype and alphabet letters (a, b, c, . . . ) on subtypes. According to the classification, HCV shows 31–35% difference between genotypes, 20–23% difference between sub- types, and 1–10% difference within even the same subtypes (Simmonds et al., *J. Gen. Virol.* 74, 661–668, 1993).

A method for analyzing HCV genotype is used in identifying infection of HCV and prognosticating infection course and treatment effect of IFN-α (Hino et al., *J. Med, Virol.* 42, 299–305, 1994). And the method for analyzing genotype is used in examining distribution and vaccine development because it shows different distribution according to the area and race (Greene et al., *J. Gen. Virol.* 76, 211–215, 1995). IFN-α is the most common antiviral agent for treating HCV. IFN-α is effective over 50% of the patients. However, only 25% of the patients may return to normally functioning liver and have no HCV in blood serum. Here, according to the study about relation between IFN-α treatment effect and HCV type, the IFN-α shows excellent treatment effect in genotypes 1a, 2, 3 and 5 but low treatment effect in genotypes 1b and 4 (Yoshioka et al., *Hepatology* 16, 293–299, 1992). In addition, genotypes 1b and 4 is rapidly transformed into chronic hepatitis while genotypes 1a and 2a is improved for the better symptom (Lopez-Labrador, et al., *J. Hepatol.* 27, 959–965, 1997).

General methods for analyzing HCV genotype are as follows. First, SSP-PCR method is to use PCR primers having specific for HCV genotype. The method is to perform RT-PCR by combining PCR primers specific for various genotypes in the core region. The method has an advantage that results can be obtained right after RT-PCR, but the method has disadvantages that new type can not be analyzed if mutations are generated around a recognition site of primers. Thus, the SSP-PCR method is not desirable in analyzing HCV genotype having diverse mutations. Second, PCR-RFLP method is to amplify a 5'UTR region by RT-PCR and use restriction enzyme (Park et el., *J. Med. Microbiol.* 47, 1998). PCR-RFLP method has an advantage that results can be easily and simply obtained, but HCV genotype are not analyzed unless the used restriction enzyme recognizes mutation region. Third, a method is to amplify a 5'UTR region by RT-PCR and hybridize an oligonucleotide probe specific on a nitrocellulose (NC) membrane for HCV genotype. According to the method, the precise results can be obtained by kinds of probe, but there is a limit in fixing a number of probes on NC membrane. In addition, the method spends a lot of time and labor in handling and analyzing various specimens because only a genotype of a person can be analyzed in the NC membrane.

SUMMARY OF THE INVENTION

Accordingly, in order to overcome the above-described problems, an object of the present invention is to provide an improved composition for analyzing HCV genotype.

Another object of the present invention is to provide an improved method for analyzing HCV genotype using the composition.

In order to accomplish the above-described objects, the present invention provides plural oligonucleotide probe compositions comprising base sequence shown in sequence ID NO: 1 to 14.

The oligonucleotide probe in the present invention is a probe for determining a HCV genotype and is fixed at a substrate.

The present invention provides a primary or secondary primer sequence shown in sequence ID NO: 15 to 20 used for detecting binding between the probe and target gene.

An anti-sense primer shown in sequence ID NO: 18 among the secondary primer is biotin-conjugated; an anti-sense primer shown in sequence ID NO: 19 among the secondary primer interacts with a fluorescent probe, and the fluorescent probe shown in sequence ID NO: 20 is cyanin-conjugated.

The present invention provides a method for analyzing HCV genotype, comprising the steps of: (a) isolating HCV RNA from blood plasma and serum; (b) performing a primary RT-PCR by using as a template, the isolated RNA, forward primer shown in sequence ID NO.15 and reverse primer shown in sequence ID NO.16; (c) performing a secondary asymmetric PCR following the primary PCR by using forward primer shown in sequence ID NO.17 and reverse primer shown in sequence ID NO.19 and fluorescent probe shown in sequence ID NO.20; (d) binding product of the secondary asymmetric PCR with the probe of claim 1; and (e) detecting the binding products.

In the method for analyzing HCV genotype in the present invention, the hybridization result is visualized using Streptavidin-Alkaline phosphatase and Nitroblue tetrazolium chloride/5-Bromo-4-chloro-3-indolyl-phosphate (NBT-BCIP) combining with biotin or a micro-array scanner.

In the present invention, a HCV oligonucleotide chip is developed for analyzing simultaneously specimens of 4 persons on a slide using a recently developed DNA microarray technology. The chip is more improved than the existing oligonucleotide chip. In order to determine HCV genotype, the present invention prepares 14 oligonucleotides which may reacts with 6 types, 11 subtypes and 53 species in HCV 5'UTR. These materials are integrated on an aldehyde glass slide having 4 chambers for 4 persons. A HCV gene amplified by RT-PCR is hybridized with a PCR by-product and an oligonucleotide probe integrated on the slide. A hybridized probe is analyzed using a chromogenic reaction or a fluorescent reaction, and 6 genotypes and 11 geno-subtypes to HCV are identified.

DETAILED DESCRIPTION OF THE PREFERRED EMBODIMENTS

Figures 1, 2:
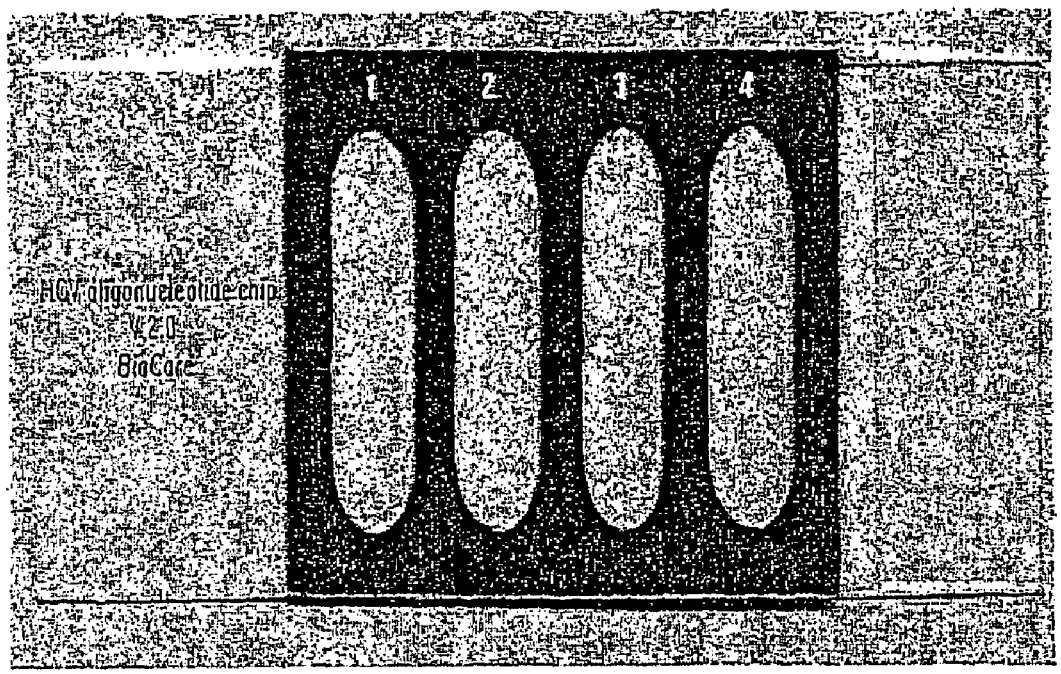
FIG. 1 is a picture showing a whole slide form of a HCV oligonucleotide chip. There are 4 chambers as shown the designated numbers to analyze simultaneously HCV genotype of 4 persons on a slide. 12 probes distinguishing HCV genotype shown in Table 5 are fixed twice on the slide and 2 probes used as positive and negative controls are fixed four times, in total of 32 probes. A HCV oligonucleotide chip is manufactured by attaching coverwell perfusion chamber (Sigma Cat# Z37916-6, USA) on the probes.
FIG. 2 is a picture showing a chromogenic reaction result on HCV 1b type of the HCV oligonucleotide chip. The picture is an image enlarging a reaction produced in one among four chambers in a slide of FIG. 1. The picture shows HCV 1b type frequently infected in Koreans. The reaction in the picture occurs simultaneously in Probes 1 and 2 among 14 probes as indicated in "reactive HCV type" in Table 5. Probe 13 is a positive control which appears in all reactions while Probe 14 is a negative control which does not appear in the all reactions, thereby confirming the precision of the experiment. Two identical spots of the same probe are fixed to make the reaction more precise. Probes 13 and 14 are twice fixed respectively on the very top and the very bottom in order to identify positive and negative controls and locations.
Figure 3:
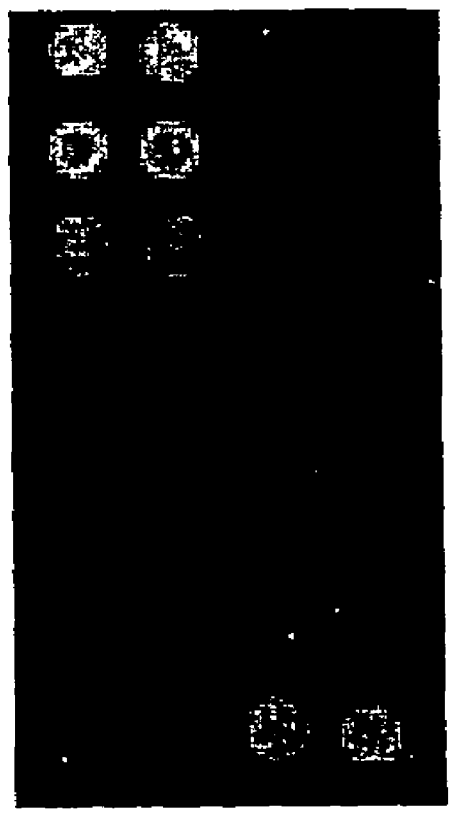
FIG. 3 is a picture showing a fluorescent reaction result on HCV 1b type of the HCV oligonucleotide chip. The reaction with probes is identical with the reaction in FIG. 2. But it is different from the reaction in FIG. 2 that fluorescent primers and probes are used in hybridization reaction and PCR reaction and a Scanner (GenePiX4000, Axon instruments, U.S.A.) is used in analyzing the reaction.

The present invention will be explained in terms of exemplary embodiments described in detail with reference to the accompanying drawings, which are given only by way of illustration and thus are not limitative of the present invention.

EXAMPLE 1

HCV Primer Synthesis and Base Sequence

A HCV PCR primer was used in RT-PCR by analyzing sites reacting in common on 6 types in 5'UTR as shown in Table 1. An anti-sense primer used in the secondary asymmetric PCR was divided into two kinds according to identifying methods. First, the primer was attached to biotin to identify the reaction with chromogenic reaction by hybridization reaction. Second, cyanin was used in identifying the reaction with fluorescent reaction by hybridization reaction. Artificially, 25 bp bases (SP6) were synthesized additionally to the 5' end of anti-sense primer for the secondary PCR and bases attached to cyanin complementary with this site were synthesized. The primers were synthesized in MWG-biotech Company (Germany) by order of inventors and the primers were synthesized by method synthesizing oligonucleotide written in 10. 42 of Molecular cloning $3^{rd}$ ed. (Sambrook and Rusell, Cold Spring Harbor Laboratory Press, New York, USA, 2001).

TABLE 1

Primer base sequence for analyzing HCV genotype

| | Primer | | Base sequence (HCV 5'UTR) | Ref. |
|---|---|---|---|---|
| Primary | Sense (sequence ID NO: 15) | | CTGTG AGGAA CTACT GTCTT | PCR Size |
| | Anti-sense (sequence ID NO: 16) | | ACTCG CAAGC ACCCT ATCAGG | 268 bp |
| Secondary | Sense (sequence ID NO: 17) | | TTCAC GCAGA AAGCG TCTAG | PCR Size |
| | Anti-sense | Chromogenic reaction | Biotin-TATCA GGCAG TACCA CAAGG (sequence ID NO: 18) | 236 bp |
| | | Fluorescent reaction | CGATT TAGGT GACAC TATAG | PCR Size |

TABLE 1-continued

Primer base sequence for analyzing HCV genotype

| Primer | Base sequence (HCV 5'UTR) | Ref. |
|---|---|---|
| | GGAGG TATCA GGCAG TACCA CAAGG (Sequence ID NO: 19) | 261 bp |
| | Cyanin-CCTTG TGGTA CTGCC TGATA CCTCC CTATA GTGTC (Sequence ID NO: 20) | Fluorescent probe |

EXAMPLE 2

Preparation of HCV RNA, Reverse Transcription-Primary PCR and Secondary PCR Reaction 1) Mixing 5 ul of HCV RNA extraction buffer (DEPC-DW 860 ul of 1 ml, Taq 10× buffer 100 ul, 1M DTT 20 ul, 10% NP40 20 ul) and 10 ul of blood plasma or serum.
2) Heating a tube with the mixed serum in a PCR device at a temperature of 92° C. for two minutes and then promptly putting the tube in ice
3) Centrifuging the tube for 5–10 seconds
4) Sequentially performing reverse transcription and primary PCR reactions in GeneAmp PCR system 9600 thermal cycler (Perkin Elmer Cetus, U.S.A.) as shown in Table 2
5) Performing the secondary asymmetric PCR reaction by using 2 ul of the primary PCR product as shown in Table 3
6) After mixing 1 ul of gel loading buffer (0.25% bromophenol blue, 0.25% xylene cyanol FF, 15% Ficoll 400) in 5 ul of the second asymmetric PCR product and performing electrophoresis with 2% agarose gel containing 1 μg/ml ethidium bromide (EtBr), identifying 236 bp or 261 bp band with Image analyzer (Vilber Lourmat, France) equipped with UV transilluminator

TABLE 2

HCV reverse transcription and primary PCR reaction condition

| Reaction composition condition | | Reaction temperature condition | | |
|---|---|---|---|---|
| DW | 16.8 | 57° C., 3.0 min. | 1 time | |
| 10 × buffer | 3.0 | 42° C., 45.0 min. | | |
| 2 mM Dntp | 1.5 | 95° C., 3.0 min. | | |
| 10 pmol primary primer | 1.5 | | | |
| 100 mM DTT | 1.5 | 94° C., 1.0 min. | 30 times | |
| 100U AMV RT | 0.3 | 52° C., 1.0 min. | | |
| 40U Rnasin | 0.3 | 72° C., 1.0 min. | | |
| 5u Taq | 0.1 | | | |
| HCV nucleic acid | 5.0 | | | |
| Total | 30 ul | 72° C., 5.0 min. | 1 time | |

TABLE 3

HCV secondary PCR reaction condition

| Reaction composition condition | | Reaction temperature condition | | |
|---|---|---|---|---|
| Sterilized D.W | 12.9 | 95° C., 3.0 min. | 1 time | |
| 10 × buffer | 2.0 | | | |
| 2 mM dNTP | 1.0 | 94° C., 1.0 min. | 25 times | |
| 1 pmol secondary sense primer | 1.0 | 53° C., 1.0 min. | | |
| 10 pmol secondary anti-sense primer | 1.0 | 72° C., 1.0 min. | | |
| 5U Taq | 0.1 | | | |
| Primary PCR product | 2.0 | | | |
| Total | 20 ul | 72° C., 5.0 min. | 1 time | |

EXAMPLE 3

Probe Synthesis and Base Sequence for Preparing HCV Oligonucleotide Chip

Amino links are attached to each 5' end of all probes for covalent bond on an aldehyde glass. 10–20 of oligo(dT) are attached to the probes to make hybridization reaction easy. Then, base sequence shown in Table 5 is attached to Amino link-Oligo(dT)$_{10-20}$. To put it shortly, the primers having an order of "Amino link-Oligo(dT)$_{10-20}$-probe base sequence" were synthesized in MWG-biotech Company (Germany) by the order from inventors. The base sequence of identified HCV genotype was identified by analyzing total 53 species of HCV gene which belongs to 6 types as shown in Table 4.

TABLE 4

The analyzed HCV genotype and classes

| HCV type | HCV classes |
|---|---|
| 1a | HCV-1(M62321), HCV-H(M67463), HC-J1(D10749), GM1(M61728), GM2(M61719), H90(M62382), US9(L38353), H77(AF009606), H99, PT-1 |
| 1b | HCV-J(D90208), HCV-BK(M58335), HCV-JK1(X61596), HCV-China(L02836), HCV-T(M84754), HCV-JT(D11168), HCV-J4/83(D13558), HCV-J4/91(D10750), HCV-JT(D11355), HCV-N(S62220), HCV-C2(D10934), HCV-L2(U01214), CON1(AJ238799), NC1(L02836), FR3(L38351), HCV-K1-S1(D50483), HCV-K1-R1(D50480), HCV-TA |
| 1c | HC-G9(D14853) |
| 2a | HC-J6(D00944), K2A(D12507), Eb-9, FR5(L38334) |
| 2b | HC-J8(D01221), MA(AB030907), K2B-1(D12509) |
| 2c | BE1369L38322) |

TABLE 4-continued

The analyzed HCV genotype and classes

| HCV type | HCV classes |
|---|---|
| 3a | NZL1(D17763), HCV-K2a(D28917), Eb-1(D10123), CB(AF046866) |
| 3b | HCV-Tr(D26556), TR-KJ(D49374) |
| 4a | GB358(L29608), ED43(Y11604), Z4(M84848), ED43(Y11604) |
| 5a | BE96(L29585), EUH1480(Y13184), BE95(L29581) |
| 6a | QC26(U33431), HK2(D43679), EUHK2(Y12083), HK |

Among base sequence shown in FIG. 5, base indicated as capital letters in the middle is the most important portion. Centering around the base, about 15–25 bp of probes were synthesized establishing about 62° C. of Tm value.

TABLE 5

Probe base sequence for determining HCV genotype

| Probe name | Base sequence | Reactive HCV type |
|---|---|---|
| HCV01(sequence ID NO: 1) | gaattgccaggaCgaccgggtcctt | 1a, 1b, 1c |
| HCV02(sequence ID NO: 2) | gccccgcGagactgct | 1b, 4a(Z4), 5a |
| HCV03(sequence ID NO: 3) | cctttcttggatTaacccgctcaat | 1c, 4a(ED43), 5a(BE95) |
| HCV04(sequence ID NO: 4) | ttggataaacccActctatgcccgg | 2a, 2c |
| HCV05(sequence ID NO: 5) | AattgccgggaAgactgggtcct | 2a |
| HCV06(sequence ID NO: 6) | acccactctatgTccggtcatttgg | 2b |
| HCV07(sequence ID NO: 7) | ctctatgcccAgccatttggg | 2c |
| HCV08(sequence ID NO: 8) | aatcgctgggGtgaccgggtc | 3a |
| HCV10(sequence ID NO: 9) | cccgcgagatCactagccgag | 3a, 3b |
| HCV11(sequence ID NO: 10) | tagtatgagtgtTgtacagcctcca | 4a |
| HCV12(sequence ID NO: 11) | gtatgagtgtcgAacagcctccagg | 5a |
| HCV13(sequence ID NO: 12) | ccgggtcctttcCattggatcaaa | 6a |
| HCV14(sequence ID NO: 13) | agtggtctgcggAaccggtgagtac | Reacting with all types (positive control) |
| HCV15(sequence ID NO: 14) | ggtctgcggGaccggtgag | No reacting with any types (negative control) |

EXAMPLE 4

Preparing HCV Oligonucleotide Chip

1) A super-aldehyde glass slide made in Telechem Co. was used in preparing an oligonucleotide chip. A probe attaching 100 pmole of the amino group was mixed with 100 pmole of DMSO. The mixed probe was fixed on a slide using Nano-plotter (NP 1.2, GeSiM, Germany). The slide is twice washed with 0.2% of SDS for 5 minutes and then twice washed with distilled water for 5 minutes. After once washed with heated distilled water in 95° C. for 2 minutes, the slide is once washed with distilled water at room temperature.
2) After the slide was reacted with sodium borohydride (1.3 g NaBH$_4$, 375 ml PBS, 125 ml 100% EtOH) for 5 minutes, the slide was three times washed with 0.2% SDS for 1 minute, once washed with distilled water for 1 minute, and then dried at room temperature.
3) To separately analyze 4 specimens on the slide, the 4 chambers were separated by attaching coverwell perfusion chamber (4 chambers) made in Sigma Company to the slide. A completed HCV oligonucleotide chip stated above was preserved in a dark place at room temperature before its use.

EXAMPLE 5

Hybridization Reaction with HCV PCR Product 1) 20–200 ul of prehybridization buffer (1% BSA, 5×SSC, 0.1% SDS) was dropped on the slide combined with oligonucleotide, and then the slide was reacted at 42° C. for 30–60 minutes. The slide was 5 times washed with distilled water, rinsed with isopropanol, dried at room temperature, and then dried at 80° C. for 2 hours.
2) In chromogenic reaction, HCV PCR product combined with biotin was denatured at 95° C. for 3 minutes, and then mixed with hybridization solution (4×SSC, 0.3% SDS) by 1:3 of ratio. In a fluorescent reaction, HCV PCR product combined with SP6 was denatured at 95° C. for 3 minutes, and then mixed with equivalent volume of cyanin-probe and hybridization solution (6×SSC, 0.5% SDS) respectively.
3) With chambers covered, 50–200 ul of hybridization buffer was filled in chambers on the slide, and then reacted at 63° C. for 1–3 hours.
4) The slide was washed using 1×SSC, 0.2% SDS at a room temperature for 5–10 minutes, washed with 0.1×SSC, 0.2% SDS at 63° C. for 5–10 minutes, washed with 0.1×SSC for 5–10 minutes, and then dried at room temperature.
5) Identifying the results
   A. Chromogenic reaction (Biotin method): The slide was reacted with 30–120 ul of blocking buffer at room temperature for 30 minutes, and then reacted with 30–120 ul of Streptavidin-Alkaline phosphatase diluted into 1/2,000 for 30 minutes. After reacting with Nitroblue tetrazolium chloride/5-Bromo-4 chloro-3-indolyl-phosphate (NBT/BCIP) diluted into 1/50 in dark place at room temperature for 1 hour, the slide was carefully washed with distilled water. HCV genotype was analyzed by indicating the color.
   B. Fluorescent reaction (Cyanin method): Fluorescent HCV genotype is analyzed with Scanner (GenePiX4000, Axon instruments, U.S.A.).

As stated above, to analyze HCV genotype, the present inventor invented method of amplifying HCV 5'UTR by PCR and analyzing base which shows different result depending on the type. Because base change in 5'UTR is defined in a specific area (Okamoto et al., *Jpn. J. Exp. Med.* 60, 215–222, 1990), the method of analyzing HCV genotype in 5'UTR has advantages that easily selected primers and made RT-PCR reaction possible on mutations or new types. In addition, because the analyzing results of HCV genotyping using 5'UTR are identical with those of core, NS3, and NS5(Karachristos et al., *J. Med. Microbiol.* 42, 367–371, 1995), the present invention analyzed HCV genotype using 5'UTR region.

As discussed earlier, in the present invention, an oligonucleotide chip was developed for diagnosing genotype by analyzing HCV 5'UTR gene. In the HCV oligonucleotide chip in the present invention, the defects of the conventional chip were solved. Two conventional probes were modified and two new probes were added. As a result, it is possible to additionally identify 1c and 2c and more precisely analyze 4a and 5a. The analysis of HCV genotype using the probes can be used as identifying HCV infection and infection course and prognosticating treatment effect of IFN-α. In addition, referring to distribution of genotype, the analysis may be used in developing HCV vaccine suitable for area and race, and it may be helpful to study chronic hepatitis, liver cirrhosis and hepatoma.

What is claimed is:

1. A composition comprising oligonucleotide probes having sequence ID NO. 1 to 14, respectively.

2. The composition according to claim 1, wherein each of the oligonucleotide probes is a probe for identifying a hepatitis C virus genotype.

3. The composition according to claim 1, wherein each of the oligonucleotide probes is immobilized on a matrix.

4. A method for analyzing a hepatitis C virus genotype, which comprises the steps of:

(a) subjecting a sample to a primary PCR stage and a secondary PCR stage, wherein the secondary PCR stage is an asymmetric PCR stage using a forward primer of sequence ID NO. 17, a reverse primer of sequence ID NO. 19 and a fluorescent probe of sequence ID NO. 20;

(b) binding a product of the secondary PCR stage with the composition of claim 1; and (c) detecting a binding result.

5. The method according to claim 4, wherein the primary PCR stage is a primary reverse transcription PCR using a forward primer of sequence ID NO. 15 and a reverse primer of sequence ID NO. 16.

6. The method according to claim 4, wherein the fluorescent probe comprises cyanin.

7. The method according to claim 4, wherein the detecting step comprises visualizing the binding result using a microarray scanner.

8. The method according to claim 4, wherein the detecting step uses streptavidin-alkaline phosphatase, nitroblue tetrazolium chloride, 5-bromo-4-chloro-3-indolyl-phosphate and biotin.

* * * * *

SEQUENCE LISTING

<160> NUMBER OF SEQ ID NOS: 20

<210> SEQ ID NO 1
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 1
gaattgccag gacgaccggg tcctt                                             25

<210> SEQ ID NO 2
<211> LENGTH: 17
<212> TYPE: DNA
<213> ORGANISM: Artificial Sequence
<220> FEATURE:
<223> OTHER INFORMATION: Probe for analyzing HCV genetic type

<400> SEQUENCE: 2
gcccccgcga gactgct                                                      17

<210> SEQ ID NO 3
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 3
cctttcttgg attaacccgc tcaat                                             25

<210> SEQ ID NO 4
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 4
ttggataaac ccactctatg cccgg                                             25

<210> SEQ ID NO 5
<211> LENGTH: 23
<212> TYPE: DNA
<213> ORGANISM: Artificial Sequence
<220> FEATURE:
<223> OTHER INFORMATION: Probe for analyzing HCV genetic type

```
<400> SEQUENCE: 5
aattgccggg aagactgggt cct                                        23

<210> SEQ ID NO 6
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 6
acccactcta tgtccggtca tttgg                                      25

<210> SEQ ID NO 7
<211> LENGTH: 21
<212> TYPE: DNA
<213> ORGANISM: Artificial Sequence
<220> FEATURE:
<223> OTHER INFORMATION: Probe for analyzing HCV genetic type

<400> SEQUENCE: 7
ctctatgccc agccatttgg g                                          21

<210> SEQ ID NO 8
<211> LENGTH: 21
<212> TYPE: DNA
<213> ORGANISM: Artificial Sequence
<220> FEATURE:
<223> OTHER INFORMATION: Probe for analyzing HCV genetic type

<400> SEQUENCE: 8
aatcgctggg gtgaccgggt c                                          21

<210> SEQ ID NO 9
<211> LENGTH: 21
<212> TYPE: DNA
<213> ORGANISM: Artificial Sequence
<220> FEATURE:
<223> OTHER INFORMATION: Probe for analyzing HCV genetic type

<400> SEQUENCE: 9
cccgcgagat cactagccga g                                          21

<210> SEQ ID NO 10
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 10
tagtatgagt gttgtacagc ctcca                                      25

<210> SEQ ID NO 11
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 11
gtatgagtgt cgaacagcct ccagg                                      25

<210> SEQ ID NO 12
```

```
<211> LENGTH: 24
<212> TYPE: DNA
<213> ORGANISM: Artificial Sequence
<220> FEATURE:
<223> OTHER INFORMATION: Probe for analyzing HCV genetic type

<400> SEQUENCE: 12
ccgggtcctt tccattggat caaa                                              24

<210> SEQ ID NO 13
<211> LENGTH: 25
<212> TYPE: DNA
<213> ORGANISM: Artificial Sequence
<220> FEATURE:
<223> OTHER INFORMATION: Probe for analyzing HCV genetic type

<400> SEQUENCE: 13
agtggtctgc ggaaccggtg agtac                                             25

<210> SEQ ID NO 14
<211> LENGTH: 19
<212> TYPE: DNA
<213> ORGANISM: Artificial Sequence
<220> FEATURE:
<223> OTHER INFORMATION: Probe for analyzing HCV genetic type

<400> SEQUENCE: 14
ggtctgcggg accggtgag                                                    19

<210> SEQ ID NO 15
<211> LENGTH: 20
<212> TYPE: DNA
<213> ORGANISM: Artificial Sequence
<220> FEATURE:
<223> OTHER INFORMATION: Primer for analyzing HCV genetic type

<400> SEQUENCE: 15
ctgtgaggaa ctactgtctt                                                   20

<210> SEQ ID NO 16
<211> LENGTH: 21
<212> TYPE: DNA
<213> ORGANISM: Artificial Sequence
<220> FEATURE:
<223> OTHER INFORMATION: Primer for analyzing HCV genetic type

<400> SEQUENCE: 16
actcgcaagc accctatcag g                                                 21

<210> SEQ ID NO 17
<211> LENGTH: 20
<212> TYPE: DNA
<213> ORGANISM: Artificial Sequence
<220> FEATURE:
<223> OTHER INFORMATION: Primer for analyzing HCV genetic type

<400> SEQUENCE: 17
ttcacgcaga aagcgtctag                                                   20

<210> SEQ ID NO 18
<211> LENGTH: 20
<212> TYPE: DNA
<213> ORGANISM: Artificial Sequence
<220> FEATURE:
<223> OTHER INFORMATION: Primer for analyzing HCV genetic type

<400> SEQUENCE: 18
```

```
tatcaggcag taccacaagg                                                    20

<210> SEQ ID NO 19
<211> LENGTH: 45
<212> TYPE: DNA
<213> ORGANISM: Artificial Sequence
<220> FEATURE:
<223> OTHER INFORMATION: Primer for analyzing HCV genetic type

<400> SEQUENCE: 19
cgatttaggt gacactatag ggaggtatca ggcagtacca caagg                        45

<210> SEQ ID NO 20
<211> LENGTH: 35
<212> TYPE: DNA
<213> ORGANISM: Artificial Sequence
<220> FEATURE:
<223> OTHER INFORMATION: Primer for analyzing HCV genetic type

<400> SEQUENCE: 20
ccttgtggta ctgcctgata cctccctata gtgtc                                   35
```